United States Patent
Katada et al.

(10) Patent No.: US 8,716,032 B2
(45) Date of Patent: May 6, 2014

(54) HIGHLY SENSITIVE IMMUNOCHROMATOGRAPHY METHOD AND KIT EMPLOYING PROTEIN HYDROLYSATES

(75) Inventors: Junichi Katada, Ashigarakami-gun (JP); Hiroyuki Chiku, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/523,388

(22) Filed: Jun. 14, 2012

(65) Prior Publication Data

US 2012/0322165 A1   Dec. 20, 2012

(30) Foreign Application Priority Data

Jun. 16, 2011 (JP) ................... 2011-134009

(51) Int. Cl.
*G01N 33/553* (2006.01)
*G01N 33/558* (2006.01)
*G01N 33/563* (2006.01)
*G01N 33/543* (2006.01)
*G01N 33/53* (2006.01)

(52) U.S. Cl.
CPC ...... *G01N 33/54393* (2013.01); *G01N 33/5308* (2013.01)
USPC ............................ 436/514; 436/513; 436/525

(58) Field of Classification Search
None
See application file for complete search history.

(56) References Cited

U.S. PATENT DOCUMENTS

| | | | |
|---|---|---|---|
| 4,818,686 A * | 4/1989 | Kortright et al. | 435/7.21 |
| 5,707,817 A * | 1/1998 | Wisnewski et al. | 435/7.22 |
| 5,989,925 A * | 11/1999 | Fitzpatrick et al. | 436/525 |
| 6,074,817 A * | 6/2000 | Landini et al. | 435/5 |
| 6,153,393 A * | 11/2000 | Seidel et al. | 435/7.1 |
| 6,368,814 B1 * | 4/2002 | Ghoshal et al. | 435/7.93 |
| 7,592,182 B2 * | 9/2009 | Milne et al. | 436/67 |
| 2003/0143530 A1 * | 7/2003 | Klepp et al. | 435/5 |

(Continued)

FOREIGN PATENT DOCUMENTS

| | | | |
|---|---|---|---|
| JP | 02-036353 A | 2/1990 | |
| JP | 06-194366 A | 7/1994 | |
| JP | 06-313766 A | 11/1994 | |
| JP | 2004-503248 A | 2/2004 | |

OTHER PUBLICATIONS

Robertson, P.W. et al., "Reduction in non-specific binding in enzyme immunoassays using casein hydrolysate in serum diluents", J. Immunological Methods (1985) 76:195-197.*

(Continued)

*Primary Examiner* — Shafiqul Haq
*Assistant Examiner* — Gary E Hollinden
(74) *Attorney, Agent, or Firm* — Sughrue Mion, PLLC

(57) ABSTRACT

The present invention is to provide an immunochromatography method which is capable of performing a detection with high-sensitivity or reduced false-positives by suppressing the occurrence of false-positive when a signal is amplified. An immunochromatography method includes in a state of where a complex of a test substance and a labeling substance containing a metal coupled with a first binding substance for the test substance is formed, developing the complex on an insoluble carrier in presence of a protease hydrolyzate of protein; capturing the test substance and the labeling substance at a detection site of the insoluble carrier containing a material which has a binding property to the first binding substance for the test substance or a second binding substance for the test substance; and detecting the test substance by amplifying the labeling substance captured.

16 Claims, 2 Drawing Sheets

(56) References Cited

U.S. PATENT DOCUMENTS

2004/0038295 A1* 2/2004 Rademacher et al. ......... 435/7.1
2008/0166821 A1* 7/2008 Oyamada et al. ............. 436/536
2009/0087927 A1 4/2009 Chiku
2010/0317048 A1* 12/2010 Fujimoto et al. ................ 435/29
2011/0136142 A1* 6/2011 Oyamada et al. .............. 435/7.9

OTHER PUBLICATIONS

Communication, dated Oct. 9, 2012, issued in corresponding EP Application No. 12171993.4, 7 pages.

* cited by examiner

HIGHLY SENSITIVE IMMUNOCHROMATOGRAPHY METHOD AND KIT EMPLOYING PROTEIN HYDROLYSATES

BACKGROUND OF THE INVENTION

1. Field of the Invention

The present invention relates to an immunochromatography method and an immunochromatography kit in which a labeled antibody is used.

2. Description of the Related Art

As a method in which a specific component in a test liquid is measured, there are many immunoassay methods which use an antigen-antibody reaction. In the immunoassay methods, there are many cases in which a non-specific reaction of the antibody or the antigen against the specific component which needs to be measured becomes a problem. Therefore, a method in which the non-specific reaction is suppressed using a blocking agent is commonly used. As methods in which the non-specific reaction is suppressed using a blocking agent, for example, a method of treating a reaction vessel with the blocking agent in the case of an ELISA or a method of treating latex particles with the blocking agent in the case of a latex agglutination method is performed (JP1994-313766A (JP-H06-313766A)). As the blocking agent, bovine serum albumin (hereinafter, abbreviated as BSA), casein, gelatin or the like is used.

Also a method of producing a carrier which suppresses the non-specific reaction using a casein treated with heat at 100° C. for 30 minutes under conditions of pH 7.2 in a system of EIA is disclosed in JP1994-194366A (JP-H06-194366A). Also, a method of suppressing the non-specific reaction by adding casein hydrolyzed to a molecular weight of approximately 1,000 to 26,000 using protease to a reaction solution in which an immunoassay is carried out is disclosed in JP1990-36353A (JP-H02-36353A).

Immunochromatography method is generally often used among immunoassay methods since the operation is simple and a sample can be measured in a short time. As an immune reaction used in immunochromatography method, a competition-type reaction or a sandwich-type reaction is widely used. Of these, in immunochromatography method, the sandwich-type reaction is standard and, in a typical example, the following operation is carried out in order to detect the test substance consisting of an antigen in a sample. First, a chromatographic carrier having a reaction site is prepared by immobilizing fine particles sensitized by an antibody with respect to an antigen which is the test substance on the chromatographic carrier as the solid-phase fine particles, or by directly immobilizing this antibody itself on the chromatographic carrier. Meanwhile, sensitized labeling fine particles are prepared by sensitizing the antibody which can specifically bind to the test substance to labeling fine particles. These sensitized labeling find particles, together with the sample, move chromatographically on the chromatographic carrier. From the above operation, the immobilized antibody becomes the immobilizing reagent in the reaction site formed in the chromatographic carrier and the sensitized labeling fine particles specifically bind to the immobilized sample through the antigen which is the test substance, and as a result, the presence, absence or the amount of the test substance in the sample may be measured by visually determining the presence, absence, or the degree of the signal generated from capturing the sensitized labeling find particles in the reaction site. Also, in immunochromatography method, adding the blocking agent such as protein to a diluted solution of analyte to suppress the non-specific adsorption is generally carried out (JP2004-503248A).

SUMMARY OF THE INVENTION

In immunochromatography method, there is a case in which a method of amplifying a detection signal is used in order to avoid a problem of not detecting an antigen (false-negative) which is a test substance due to low sensitivity. As the method of signal amplification, an enzyme such as alkaline phosphatase or peroxidase may be used as a label, however, a method of carrying out detection by sensitization using a silver-containing compound and a reducing agent for silver ions as a label selected from the group consisting of colloidal metal labels and metal sulfide labels (silver amplification) may also be used. However, when these amplification methods are used, there is a problem of detecting a signal even when the antigen which is the test material is not present (false-positive) if a label non-specifically adsorbed to the detection site is sensitized. In particular, in immunochromatography method which uses signal amplification, a problem of false-positives is caused even with a small amount of non-specific adsorption which has not been a problem in the related art.

Also, in immunochromatography method, adding blocking agents such as a protein to the diluted solution of analyte to suppress the non-specific adsorption is generally carried out (JP2004-503248A), however, none is effective for such a small amount of non-specific adsorption.

Also, when conducting immunochromatography method using silver amplification, it is necessary that, after the analyte is added dropwise on an immunochromatography strip using the colloidal metal labeling substance and the metal sulfide labeling substance, and are developed, (1) the reducing agent solution will be developed, and (2) the silver-containing solution (the silver amplification liquid) will be added dropwise. Regarding the silver amplification solution, an acidic solution is usually suitable for the stability of silver ions and amplification activity. Protein, on the other hand, precipitates when protein is added to the silver amplification liquid since the protein is often precipitated under the acidic condition. Therefore, in a case in which the protein is added to the diluted solution of analyte, the protein is aggregated on a membrane and interrupts the flow of the liquid in certain places under the acidic condition, and as a result, unevenness after the amplification occurs. The amplification unevenness is a major problem since it might be indistinguishable from a color formation in the detection site and might become a false-positive.

The problem to be solved by the present invention is to provide an immunochromatography method in which detection with high-sensitivity or reduced false-positives may be performed by suppressing the occurrence of false-positives when a signal is amplified using an immunochromatography method.

The inventors, as a result of intensive studies to solve the problem described above, found that false-positives after the amplification may be suppressed by suppressing a non-specific adsorption of a label by carrying out an immune reaction under the presence of a protease hydrolyzate of protein such as casein.

According to the present invention, an immunochromatography method includes: in a state where a complex of a test substance and a labeling substance containing a metal coupled with a first binding substance for the test substance is formed, developing the complex on an insoluble carrier in presence of a protease hydrolyzate of protein; capturing the test substance and the labeling substance at a detection site of the insoluble carrier containing a material which has a binding property to the first binding substance for the test substance or a second binding substance for the test substance; and detecting the test substance by amplifying the labeling substance captured.

It is preferable that a molecular weight range of the protease hydrolyzate of protein be 0.1 kD to 15 kD.

It is preferable that the protease hydrolyzate of protein be a hydrolyzate which does not precipitate insoluble components under the acidic condition.

It is preferable that the protease hydrolyzate of protein be a protein hydrolyzate obtained by adding an acid to the protease hydrolyzate of protein, adjusting a pH to 4 or less and removing the precipitates precipitated.

It is preferable that the protease hydrolyzate of protein be a protease hydrolyzate of casein.

It is preferable that the casein used as the protein be one or more casein selected from αS1casein, αS2casein, βcasein, or κcasein.

It is preferable that at least one or more of αS1 casein derived peptide sequences (YLGYLEQLLR (SEQ ID NO: 1), FFVAPFPEVFGK (SEQ ID NO: 2), HQGLPQEVLNNLLR (SEQ ID NO: 3)), αS2 casein derived peptide sequence (FALPQYLK) (SEQ ID NO: 4), β casein derived peptide sequences (AVPYPQR (SEQ ID NO: 5), YPVEPFTER (SEQ ID NO: 6)), or κ casein derived peptide sequence (YIPIQYVLSR) (SEQ ID NO: 7) be included in the protease hydrolyzate of casein.

It is preferable that the insoluble carrier be a porous carrier.

It is preferable that the labeling substance containing metal be a colloidal metal.

It is preferable that the colloidal metal be colloidal gold.

It is preferable that at least one of the first binding substance and the second binding substance be an antibody.

It is preferable that amplifying the labeling substance captured be performed by using amplification liquid containing a silver-containing compound and a reducing agent for silver ions.

It is preferable that in a state where the complex of the test substance and a labeling substance containing a metal coupled with a first binding substance for the test substance is formed, developing the complex on the insoluble carrier in presence of a protease hydrolyzate of protein, and amplifying the labeling substance captured.

It is preferable that, at the time of the detection, the labeling substance having an average particle size of greater than or equal to 1 µm and less than or equal to 20 µm be detected.

Also, according to the present invention, the immunochromatography kit includes a labeling substance containing a metal modified with a first binding substance with respect to a test substance and an insoluble carrier containing a second binding substance with respect to the test substance or a substance which has a binding property to a first binding substance with respect to the test substance.

It is preferable that at least one of the first binding substance and the second binding substance be an antibody.

According to the present invention, a measurement with clarity and high sensitivity may be carried out by suppressing the occurrence of false-positives after the amplification in silver amplification of the immunochromatography method.

BRIEF DESCRIPTION OF THE DRAWINGS

In FIG. 1 and FIG. 2, 1 represents a back adhesive sheet, 2 represents a labeling substance holding pad, 3 represents a chromatographic carrier (an antibody immobilized membrane), 3a represents a capture site, 31 represents a detection site, 32 represents a control site, 4 represents an absorption pad, 5 represents a sample addition pad, and 10 represents an immunochromatography strip. The direction of a test sample containing a test substance being developed on the immunochromatography carrier is represented as an arrow A. In the present invention, the base direction of the arrow A is defined as upstream and the tip direction of the arrow A is defined as downstream.

FIG. 2, 52 represents a liquid storage pod, 53 represents a second insoluble carrier (a cleaning liquid addition pad), 54 represents a third insoluble carrier, 55 represents a first device component, 56 represents a second device component, and 57 represents an adhesion hole.

DESCRIPTION OF THE PREFERRED EMBODIMENTS

Figure 1:
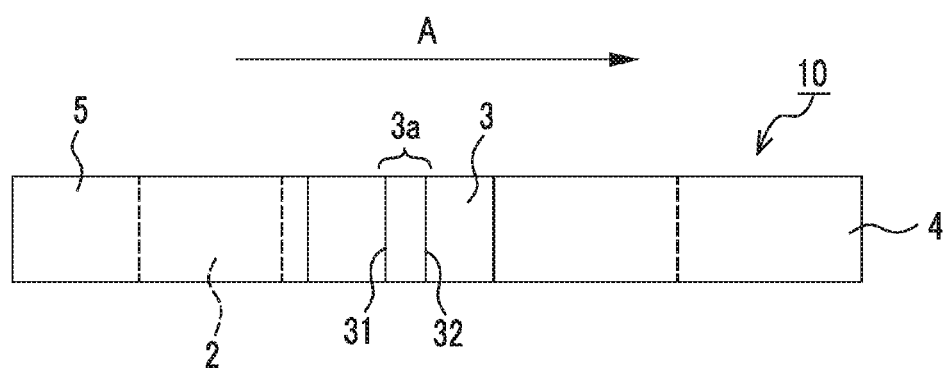
FIG. 1 is a plane diagram schematically showing one aspect of a first insoluble carrier (an immunochromatography strip).

Hereinafter, the present invention is described in more detail.

In the immunochromatography method of the present invention, in a state where a complex of a test substance and a labeling substance containing a metal coupled with a first binding substance for the test substance is formed, developing the complex on an insoluble carrier in presence of a protease hydrolyzate of protein.

As the method in which the complex is developed on the insoluble carrier in the presence of a protease hydrolyzate of protein, any method in which the protease hydrolyzate of protein flows together with a test sample containing a test substance when the test sample containing the test substance is flowed may be used. As an aspect used, a method in which the solution including the test sample containing the test substance and the protease hydrolyzate of protein is developed on the insoluble carrier and the like may be used.

The range of the molecular weight of the protease hydrolyzate of protein is preferably 0.1 kD to 15 kD and particularly preferably 1 kD to 15 kD. As a method of measuring the molecular weight of the protease hydrolyzate of protein and the content ratio thereof, a gel electrophoresis method often used in the art in which the protein is separated by molecular weight and stained with a staining solution, the stained band is imaged, and an actual value of the concentration is determined and the like may be used. The range of the molecular weight of the protease hydrolyzate of protein in the present invention means a range of the molecular weight containing 50% or more among the total protein amount by the molecular weight and the content ratio being determined using the method described above.

When the protease hydrolyzate of protein is used, precipitating even under the acidic condition becomes difficult since the molecular weight becomes smaller, however, the precipitates formed can be the cause of unevenness after amplification. In the present invention, it is preferable that the insoluble component in an acidic condition contained in the protein hydrolyzate be removed in advance. That is, as the protease hydrolyzate of protein used in the present invention, a hydrolyzate which does not substantially precipitate the insoluble component under the acidic condition is preferable. A hydrolyzate which does not precipitate the insoluble component with the concentration of 1 g/5 ml in a water solution of pH 4 at 20° C. is more preferable. For example, the protein hydrolyzate in which the acidic insoluble substance obtained as precipitates by adjusting the pH to 4 or less by adding an acid to the protease hydrolyzate of protein is removed may be used as the protease hydrolyzate of protein. As the method of removing the precipitates, a method such as decantation, ultracentrifugation, or filtration may be chosen.

As the type of protein, casein, gelatin, bovine serum albumin or the like is preferably used and casein is more preferably used in order to achieve an effect of the present invention.

As the type of casein used in the present invention, one or more casein selected from αS1casein, αS2 casein, β casein, or κ casein is preferably used.

Examples of the protease hydrolyzate of casein which may be used in the present invention include, at least one of αS1 casein derived peptide sequences (YLGYLEQLLR (SEQ ID NO: 1), FFVAPFPEVFGK (SEQ ID NO: 2), HQGLPQEVLNNLLR (SEQ ID NO: 3)), αS2 casein derived peptide sequence (FALPQYLK) (SEQ ID NO: 4), β casein derived peptide sequences (AVPYPQR (SEQ ID NO: 5), YPVEPFTER (SEQ ID NO: 6)), or κ casein derived peptide sequence (YIPIQYVLSR) (SEQ ID NO: 7).

1. Chromatograph

In general, a chromatography method is a method which simply, quickly, and specifically determines and measures a test substance in the following manner. That is, a chromatographic carrier (an insoluble carrier) having at least one reaction site including a immobilizing reagent (antibody, antigen, and the like) which is the second binding substance capable of binding to the test substance is used as a stationary phase. On this chromatographic carrier, a dispersion liquid formed from dispersing the labeling substance modified by the reagent which is the first binding substance capable of binding to the test substance is used as a mobile phase, and along with the mobile phase moving through the chromatographic carrier chromatographically, the test substance and the labeling substance specifically bind and reach the reaction site. It is a method which uses the fact that the labeling substance is concentrated on the immobilizing reagent site only when the test substance is present in the test sample by the complex of the test substance and the labeling substance specifically binding to the immobilizing reagent in the reaction site and qualitatively and quantitatively analyzes the presence of the test substance in the test sample visually or using a suitable device.

A kit or apparatus which carries out the chromatography method in the present invention preferably includes the silver-containing compound and the reducing agent for silver ions inside, and by amplifying the signal from an amplification reaction in which the complex of the test substance and the labeling substance which binds to the immobilizing reagent is made to be a core, high-sensitivity may be achieved as a result. According to the present invention, quick and highly sensitive chromatography may be performed.

2. Test Sample

The test sample which can be analyzed using the chromatography method of the present invention is not particularly limited as long as the sample contains the test substance and, for example, a biological sample, particularly body fluid of an animal (particularly a human) (for example, blood, serum, plasma, cerebrospinal fluid, lacrimal fluid, sweat, urine, pus, nasal discharge, or sputum) or an excretion (for example, excrement), organ, tissue, mucous membrane or skin, abraded analyte considered to contain these (swab), gargle liquid, or animals and plants themselves or dried bodies thereof may be included.

3. Pretreatment of Test Sample

In the chromatography method of the present invention, the test sample may be used as it is, or as a form of extracted solution obtained from extracting the test sample using a suitable extracting solvent, furthermore, as a form of diluted solution obtained from diluting the extracted solution using a suitable diluting agent, or as a concentrated form of the extracted solution using a suitable method. As the extracting solvent, a solvent used in conventional immunological analysis (for example, water, physiological sodium chloride solution, buffer solution or the like) or a water-miscible organic solution in which the antigen-antibody reaction may be directly carried out by being diluted with the solvent may be used.

4. Configuration

Figure 2:
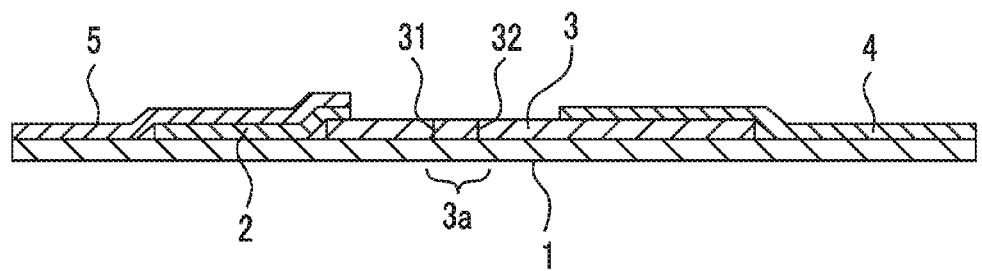
FIG. 2 is a schematic diagram showing a longitudinal section of one aspect of the first insoluble carrier (the immunochromatography strip) shown in FIG. 1.

As the chromatographic strip which can be used in the chromatography method of the present invention, along the direction of the test sample being developed (the direction of arrow A in FIG. 1), the sample addition pad, the labeling material holding pad (for example, colloidal gold antibody holding pad), the chromatographic carrier (the insoluble carrier, for example, the antibody immobilized membrane) and the absorption pad may be arranged on the back adhesive sheet in this order as shown in FIG. 1 and FIG. 2. The chromatographic carrier includes a capture site and a detection site (also may be described as a detection zone), which is an area in which the antibody or the antigen specifically bound to an analyte is immobilized, and may further include a control site (also may be described as a control zone), which is an area in which the antibody or the antigen for control is immobilized if desired. The labeling substance holding pad may be prepared by preparing a suspension containing the labeling substance, coating the suspension on a suitable absorption pad (for example, a glass fiber pad), and then drying it. As the sample addition pad, a glass fiber pad may be preferably used in the present invention.

4-1. Labeling Substance

The labeling substance used in the present invention is a label used to label the first binding substance which specifically binds to the test substance (antigen) and a labeling substance containing metal may be used. As the types of metal which can be used in the present invention, precious metal of gold, silver, or platinum, iron, lead, copper, cadmium, bismuth, antimony, tin or mercury may be preferably used and precious metal of gold, silver, or platinum may be more preferably used. As a preferable form of the labeling substance containing metal which can be used in the present invention, the colloidal metal label or the metal sulfide label may be used. In the present invention, as the colloidal metal label, colloidal platinum, colloidal gold, colloidal silver, colloidal iron, or colloidal aluminum hydroxide or the like may be used and as the metal sulfide label, each sulfide of iron, silver, lead, copper, cadmium, bismuth, antimony, tin or mercury may be preferably used. In the present invention, colloidal platinum, colloidal gold, or colloidal silver may be more preferably used. In the immunochromatography method of the present invention, one or more of these colloidal metal labels and/or metal sulfide labels thereof may be used as the label. The binding of the colloidal metal with specific binding substance may be carried out according to known methods in the related art (for example, The Journal of Histochemistry and Cytochemistry, Vol. 30, No. 7, pp 691-696 (1982)).

4-2. Binding Substance

In the present invention, the labeling substance is modified with the first binding substance with respect to the test substance. As the first binding substance, for example, a compound having an affinity for the test substance such as an antibody against the test substance (antigen), an antigen against the test substance (antibody), an aptamer against the test substance (protein, low-molecular compound or the like) may be used.

In the present invention, the insoluble carrier has (a) the second binding substance with respect to the test substance or (b) the substance having a binding property to the first binding substance. As the second binding substance with respect to the test substance, for example, a compound having an affinity for the test substance such as an antibody against the test substance (antigen), an antigen against the test substance (antibody), an aptamer against the test substance (protein, low molecular compound or the like) may be used. Also the second binding substance may be different from or the same as the first binding substance. The substance having a binding property to the first binding substance with respect to the test substance may be the test substance itself, the compound having a site which the first binding substance recognizes and, for example, a compound in which a derivative of the test substance and protein (for example, BSA or the like) are bound may be included.

In the present invention, it is preferable that at least any one of the first binding substance and the second binding substance be an antibody. In the immunochromatography method of the present invention, as the antibody which has specificity with respect to the test substance, an antiserum prepared from a serum of an animal immunized by the test substance, an immune globulin fraction purified from the antiserum, a monoclonal antibody obtained by cell fusion which uses spleen cells of an animal immunized by the analyte or fragments thereof [for example, F (ab')$_2$, Fab, Fab', or Fv] may be preferably used. The preparation of these antibodies may be performed by common methods.

4-3. Chromatographic Carrier (Antibody Immobilized Membrane)

As the chromatographic carrier, an insoluble carrier may be used and a porous carrier among them is preferable. In particular, a nitrocellulose membrane, a cellulose membrane, an acetyl cellulose membrane, a polysulfone membrane, a polyethersulfone membrane, a nylon membrane, glass fiber, non-woven fabrics, a cloth, a thread or the like may be preferably used.

The detection site is usually prepared by immobilizing the immobilizing reagent on parts of the chromatographic carrier. The immobilizing reagent may be directly immobilized on parts of the chromatographic carrier by physical or chemical binding or the immobilizing reagent may be physically or chemically bound on fine particles such as latex particles and fine particles are trapped in parts of the chromatographic carrier and immobilized. Also, it is preferable that, after the immobilizing reagent is immobilized, the chromatographic carrier be treated for non-specific adsorption prevention by a treatment using an inactive protein and the like and used.

4-4. Sample Addition Pad

The material of a sample addition pad may include a material having uniform properties such as cellulose filter paper, glass fiber, polyurethane, polyacetate, cellulose acetate, nylon and cotton cloth, however, is not limited to these. The sample adding unit not only accepts the test sample containing the test substance added but also has a function to filter insoluble particles and the like in the sample. Also, in order to prevent the non-specific adsorption of the test substance in the test sample to the material of the test sample adding unit and lowering the degree of accuracy of the analysis at the time of the analysis, the material composed of the sample adding unit is sometimes treated for non-specific adsorption prevention in advance and used.

4-5. Labeling Substance Holding Pad

As the material of the labeling substance holding pad, for example, cellulose filter paper, glass fibers, non-woven cloth and the like may be included and it is produced by a certain amount of the labeling substance prepared as described above being impregnated and dried.

4-6. Absorption Pad

An absorption pad is a site which absorbs and removes the unreacted labeling substance and the like which does not become insoluble in the detecting unit of the chromatographic carrier along with physically absorbing the added sample by chromatographic development, and an absorbent material such as cellulose filter paper, non-woven cloth, a cloth, cellulose acetate or the like is used. The speed of the chromatography after tip of the chromatographed added sample reaches the absorbing unit depends on the material, size or the like of the absorber, therefore, the speed that matches the measurement of the test substance may be set by the selection.

5. Method of Immunity Test

Hereinafter, the sandwich-type method as the specific embodiment according to the chromatography method of the present invention is described.

In the sandwich-type method, while not particularly limited, for example, an analysis of the test substance may be carried out according to the following procedure. First, the first antibody and the second antibody having specificity with respect to the test substance (antigen) are prepared in advance by the method described above in 4-2. Also, the first antibody is labeled in advance using the method described in 4-1 or 4-2. The second antibody is immobilized on the appropriate first insoluble carrier (for example, a nitrocellulose membrane, a glass fiber membrane, a nylon membrane, a cellulose membrane or the like) and is brought into contact with the test sample (or the extracted solution thereof) which has a possibility of containing the test substance (antigen), and an antigen-antibody reaction occurs if the test substance is present in the test sample. This antigen-antibody reaction may be performed in a same manner as conventional antigen-antibody reactions. When an excess of the labeled first antigen is further brought into contact at the same time as or after this antigen-antibody reaction, the immune complex made of the immobilized second antigen, the test substance (antigen) and the labeled first antibody are formed if the test substance is present in the test sample.

In the sandwich-type method, the reaction of the immobilized second antigen and the test substance (antigen) with the first antibody is completed, the labeled first antigen which did not form the immune complex is removed, and subsequently the labeling substance is quantified by carrying out a first optical density measurement of the area which immobilizes the immobilized second antigen in the first insoluble carrier, and the amount of the test substance in the test sample may be measured. Then, after the signal from the label of the labeled first antigen which forms the immune complex by supplying metal ions and a reducing agent is amplified, the labeling substance after the amplification may be quantitated by carrying out a second optical density measurement and then the amount of the test substance in the test sample may be measured.

6. Cleaning

In the present invention, in the state of forming the complex from the test substance and the labeling substance containing the metal modified with the first binding substance with respect to the test substance, a cleaning liquid is developed on the insoluble carrier after developing the complex on the insoluble carrier in presence of the protease hydrolyzate of protein, and the labeling substance captured can be amplified.

(Cleaning Liquid)

A cleaning liquid with a function of removing the labeling substance which does not form the immune complex can be any liquid as long as it has a function of cleaning.

The cleaning liquid is not particularly limited as long as it is a liquid to clean the labeling substance remaining on the chromatographic carrier which is not bound by the specific binding reaction, that is, remaining non-specifically, and a single solvent such as simple water or ethanol or, for example, a solution such as PBS buffer containing 1 mass % of BSA or a surfactant or the like may be used. Also, a liquid containing silver ions or a liquid containing a reducing agent of silver ions described later may be used as the cleaning liquid. Also, the cleaning liquid is developed while including the labeling substance since it is developed while cleaning the labeling substance remaining non-specifically during developing, however, a liquid which does not include the labeling substance is used as the cleaning liquid before developing to enhance the cleaning effect. Also, the cleaning liquid in which the pH is adjusted or protein such as a surfactant component or BSA or a polymer compound such as polyethylene glycol is added to enhance the cleaning effect may be used.

(Development of the Cleaning Liquid, the Direction)

The cleaning liquid is added to the chromatographic strip after the analyte solution is developed and cleans the labeling substance which remained in the chromatographic strip and is not bound by antigen-antibody reaction. As the liquid delivery method of the cleaning liquid, a method in which the cleaning liquid is added to the sample dropping unit as it is after the analyte solution is developed, a method in which the cleaning liquid addition pad for delivering liquid of the cleaning liquid and the absorption pad are attached to the strip in advance and the liquid is added to the cleaning liquid addition pad and delivered in the direction of the absorption pad, a method in which the adding site of the cleaning liquid is prepared in the strip in advance and the cleaning liquid is added to the adding site of the cleaning liquid after the analyte solution is developed or the like may be included, however, it is more preferable that a method be used in which the cleaning liquid addition pad for delivering liquid of the cleaning liquid and the absorption pad are attached to the strip after the analyte solution is developed to the strip, the cleaning liquid is supplied to the cleaning liquid addition pad, and the cleaning liquid is developed. As the method in which the cleaning liquid is supplied to the cleaning liquid addition pad, the cleaning liquid addition pad may be put into a pot containing the cleaning liquid or the cleaning liquid may be added dropwise to the cleaning liquid addition pad.

In the present specification, a developing direction of the test substance solution is defined as the direction which connects the sample addition pad and the absorption pad and the developing direction of the cleaning liquid is defined as the direction which connects the cleaning liquid addition pad to deliver liquid of the cleaning liquid and the absorption pad.

The cleaning effect becomes large when an angle formed between the developing direction of the test substance solution and the developing direction of the cleaning liquid is from 45 degrees to 170 degrees. Also, the angle formed between the developing direction of the test substance solution and the developing direction of the cleaning liquid is preferably from 60 degrees to 170 degrees, and more preferably from 60 degrees to 150 degrees.

As the cleaning liquid addition pad (also written as the second insoluble carrier) in the present invention, a glass fiber pad, a cellulose membrane, a nitrocellulose membrane or the like may be used.

As the absorption pad (also written as the third insoluble carrier) in the present invention, cellulose, nitrocellulose, glass fibers, a mixture thereof or the like may be used.

7. Amplification Liquid

An amplification liquid is a solution in which contained chemicals is catalytically reacted by an action of the labeling substance or the test substance and therefore generates a colored compound, luminescence or the like and may cause an amplification of the signal. For example, a silver ion solution which causes a precipitation of the metallic silver by a physical development or a solution of a phenylenediamine compound and a naphthol compound which becomes a dye by an action of a peroxidase label and hydrogen peroxide may be included.

In detail, a so-called photographic-developer described in general books in the field of photochemistry (for example, "Principles of Photographic Science and Engineering (revised), —Silver Salt Photography—" (The Society of Photography and Imaging of Japan, Corona Publishing Co., Ltd.), "Chemistry of Photography" (Akira Sasai, Photographic Industry Publication, Co., Ltd.) "Latest Prescription Handbook" (Shinichi Kikuchi et al., Amico Publishing Company) may be used, and a so-called physical photographic-developer which includes silver ions in the solution and is reduced with the colloidal metal or the like in which the silver ions in the solution becomes a core of the development as a center may be used as the amplification liquid without being particularly limited.

Specific examples of the amplification liquid which may be used include an amplification liquid containing the silver-containing compound and the reducing agent for silver ions. The amplification liquid in the present invention may be prepared and used as one amplification liquid containing the silver-containing compound and the reducing agent for silver ions together, however, as a preferable aspect of the present invention, it is preferable that an amplification liquid containing the silver-containing compound and an amplification liquid containing the reducing agent for silver ions be separately prepared and used. Hereinafter, the silver-containing compound and the reducing agent for silver ions and the like are described.

(Silver (Ion)-Containing Compound)

As the silver-containing compound, an organic silver salt, an inorganic silver salt or a silver complex may be used. The silver ion-containing compound with high-solubility in solvents such as water is preferable, and silver nitrate, silver acetate, silver lactate, silver butyrate, silver thiosulfate or the like may be included. Silver nitrate is particularly preferable. As the silver complex, a silver complex coordinated to a ligand having a water-soluble group such as a hydroxyl group or a sulfonic group is preferable, and silver hydroxy thioether or the like may be included.

It is preferable that the organic silver salt, the inorganic silver salt or the silver complex be contained generally at $0.001$ mol/$m^2$ to $0.2$ mol/$m^2$ as silver and preferably at $0.01$ mol/$m^2$ to $0.05$ mol/$m^2$ as silver.

(Reducing Agent for Silver Ions)

A reducing agent for silver ions used may be any organic or inorganic material or a mixture thereof as long as the silver ions are reduced to silver.

As the inorganic reducing agent, a reducing metal salt or a reducing metal complex salt capable of changing the valence of a metal ion such as $Fe^{2+}$, $V^{2+}$, $Ti^{3+}$ or the like may be preferably included. When using the inorganic reducing agent, it is necessary that the ion oxidized is either removed or made to be harmless by complex formation or reduction. For example, in a system in which $Fe^{2+}$ is used as the reducing agent, $Fe^{2+}$ may be made to be harmless by forming a complex of $Fe^{3+}$ which is an oxide, using citric acid or EDTA. In the present system, using the inorganic reducing agent such as this is preferable and the metal salt of $Fe^{2+}$ is more preferable.

Also, the main developing agent used in a wet silver halide photosensitive material (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or a derivative thereof), and leuco dyes) and other materials which are apparent for those skilled in the related art, for example, materials disclosed in U.S. Pat. No. 6,020,117 may be used.

As the reducing agent, an ascorbic acid reducing agent is preferable. Useful ascorbic reducing agents include ascorbic acid and analogs, isomers, and derivatives thereof and, for example, D- or L-ascorbic acid and sugar derivatives thereof (for example, γ-lactoascorbic acid, glucoascorbic acid, fucoascorbic acid, glucoheptoascorbic acid, maltoascorbic acid), sodium ascorbate, potassium ascorbate, isoascorbic acid (or L-erythroascorbic acid), salts thereof (for example, alkali metal salts, ammonium salts, or salts known in the related art), enediol-type ascorbic acid, enaminol-type ascorbic acid, thioenol-type ascorbic acid or the like may be preferably included. In particular, D-, L-, or D,L-ascorbic acid (and alkali metal salts thereof) or isoascorbic acid (or alkali metal salts thereof) is preferable and a sodium salt is a preferable salt. A mixture of these reducing agents may be used as necessary.

8. Other auxiliaries

As other auxiliaries of the amplification liquid, a buffering agent, a preservative, for example, an antioxidant or an organic stabilizer, or a speed adjusting agent may be included. As the buffering agent, for example, a buffering agent which uses acetic acid, citric acid, sodium hydroxide or a salt of any of these or tris(hydroxymethyl)aminomethane, or other buffering agents used in general chemical experiments may be used. These buffering agents are used appropriately and the pH may be adjusted to be optimized as the amplification liquid. Also, an alkylamine as an antifogging agent may be used as an additive and dodecylamine is particularly preferable. Also, in order to enhance the solubility of these additives, the surfactant may be used and $C_9H_9-C_6H_4-O-(CH_2CH_2O)_{50}H$ is particularly preferable.

9. An Immunochromatography Kit

The immunochromatography method according to the present invention can be conducted using an immunochromatography kit, comprising, a labeling substance containing a metal modified with a first binding substance for a test substance, a protease hydrolyzate of protein, and an insoluble carrier containing a second binding substance for the test substance or a substance which has a binding property to the first binding substance for the test substance. The immunochromatography kit may contain, an insoluble carrier developed with a labeling substance containing a metal modified with a first binding substance for the test substance and a protease hydrolyzate of protein. Or else, an insoluble carrier may be developed with at least a labeling substance containing a metal modified with a first binding substance for the test substance and a protease hydrolyzate of protein. In this instance, measurement will be conducted using a method such that mixing and developing a test substance and other substances to the insoluble carrier when measuring. Moreover, the immunochromatography kit according to the present invention may further comprise an amplification liquid containing a silver-containing compound and a reducing agent for silver ions. The preferable component used for the immunochromatography kit may be selected from the examples and scopes as mentioned above.

10. Method of Calculating Average Particle Size at the Time of Detection

At the time of the detection (after the amplification), after a test line unit is cut off and a back side of the sample is attached to a sample holder using carbon paste, a cross section is cut, carbon is evaporated and the shape and size is observed using a scanning electron microscope. For example, an SEM reelection electron observation of the sample surface with accelerating voltage of 10 kV using a FE-STEM S-5500 manufactured by Hitachi High-Technologies Corporation may be performed. After that, 100 signal particles are selected, a circle equivalent particle diameter of the projected area of the particles is measured, an average value is calculated, and the value is made to be the average particle size at the time of the detection.

The present invention is more specifically described by the following examples, however, the present invention is not limited to these examples.

EXAMPLES (1) Preparation of Immunochromatography Kit for Influenza Type A Detection (1-1) Preparation of Colloidal Gold Modified by Anti-Influenza Type A Antibody (1-1-1) Preparation of F(ab')$_2$ Fragmented Anti-Influenza Type A Virus Antibody It was prepared using an anti-influenza type A virus antibody (Product No. 7307, Medix Biochemica) and an ImmunoPureIgGI Faband F(ab')$_2$ Preparation kit (Product No. 44880, Pierce, Inc.).

(1-1-2) Preparation of Colloidal Gold Modified by Anti-Influenza Type A Fragmented Antibody 1 mL of F(ab')$_2$ fragmented anti-influenza type A virus antibody solution made from (1-1-1) with a concentration of 160 μg/mL was added to the colloidal gold solution of which the pH was adjusted by adding 1 mL of 50 mM $KH_2PO_4$ buffer (pH 7.5) to 9 mL of colloidal gold solution with a diameter of 50 nm (EM. GC50, BBI Corporation) and the mixture was stirred. After standing for 10 minutes, 550 μL of 1 mass % aqueous solution of polyethylene glycol (PEG Mw. 20,000, Product No. 168-11285, Wako Pure Chemical Industries, Ltd.) was added and the mixture was stirred, and subsequently 1.1 mL of 10 mass % aqueous solution of bovine serum albumin (BSA FractionV, Product No. A-7906, SIGMA) was added and the mixture was stirred. After this solution was centrifuged (HimacCF16RX, Hitachi, Ltd.) for 30 minutes under the condition of 8,000×g and 4° C., supernatant was removed leaving approximately 1 mL and the colloidal gold was re-dispersed using an ultrasonic cleaner. After that, the resultant was dispersed to 20 mL of colloidal gold preservative solution (20 mM Tris-HCl buffer (pH 8.2), 0.05 mass % PEG (Mw. 20,000), 150 mM NaCl, 1 mass % BSA, 0.1 mass % $NaN_3$), was centrifuged again for 30 minutes under the condition of 8,000×g and 4° C., supernatant was removed leaving approximately 1 mL and the colloidal gold was re-dispersed using an ultrasonic cleaner and the solution of colloidal gold modified by the antibody (50 nm) was obtained.

(1-2) Preparation of Colloidal Gold Antibody Holding Pad (Labeling Substance Holding Pad)

Colloidal gold modified by anti-influenza type A antibody made from (1-1) was diluted by colloidal gold coating liquid (20 mM Tris-HCl buffer (pH 8.2), 0.05 mass % PEG (Mw. 20,000), 5 mass % sucrose) and water, and was diluted so that the optical density (OD) at 520 nm became 3.0. This solution was uniformly coated on the glass fiber pad (Glass Fiber Conjugate Pad, Millipore Corporation) which was cut into 8 mm×150 mm with 0.8 mL per each pad, dried under reduced pressure for 12 hours, and the colloidal gold antibody holding pad was obtained.

(1-3) Preparation of Antibody Immobilized Membrane (Chromatographic Carrier)

An antibody immobilized membrane was made by immobilizing the antibody according to the following method with respect to the nitrocellulose membrane which was cut into 25 mm×200 mm (using a plastic backing, HiFlow Plus HF120, Millipore Corporation). The membrane was set up widthways, and at the position of 10 mm along the length side of 200 mm, the solution of anti-influenza type A virus antibody (Product No. 7307, Medix Biochemica) prepared to be 1.5 mg/mL was coated as a line shape with a width of approximately 0.7 mm using an ink jet type coater (BioDot, Inc.) and was set as the detection site. Also, in the same manner, at the position of 16 mm along the length side of 200 mm (the position of 6 mm away from the detection site), the solution of anti-mouse IgG antibody for the control (anti-mouse IgG (H+L), rabbit F(ab')$_2$, Product No. 566-70621, Wako Pure Chemical Industries, Ltd.) prepared to be 0.5 mg/mL was coated as a line shape and was set as the control site. The coated membrane was dried for 30 minutes at 50° C. using a warm air dryer. 500 mL of blocking liquid (50 mM boric acid buffer (pH 8.5) containing 0.5 mass % casein (derived from milk, Product No. 030-01505, Wako Pure Chemical Industries, Ltd.)) was placed in a vat and was left to stand for 30 minutes intactly with the nitrocellulose membrane of which drying has been completed being immersed. After that, the membrane was transferred and immersed in 500 mL of cleaning and stabilizing liquid (50 mM Tris-HCl (pH 7.5) buffer containing 0.5 mass % sucrose and 0.05 mass % sodium cholate) placed in a similar vat and was left to stand for 30 minutes intactly. After that, the antibody immobilized membrane was prepared by taking out the membrane from the liquid and drying for 12 hours at room temperature.

(1-4) Preparation of the Immunochromatography Strip

The antibody immobilized membrane made from (1-3) was grafted to the back adhesive sheet (ARcare9020, NIPPN/TechnoCluster, Inc.) and the membrane of 25 mm×200 mm was installed in withways. The colloidal gold antibody holding pad (labeling substance holding pad) prepared by 1-2 was grafted in widthways so that the control site of the installed membrane overlapped by approximately 2 mm with the end of the long side of the membrane corresponding to the side of the detection site. Also, the sample addition pad (a glass fiber pad cut into 18 mm×250 mm (Glass Fiber Conjugate Pad, Millipore Corporation)) was grafted overlapping in widthways by approximately 4 mm with the colloidal gold antibody holding pad to a position to the opposite side of the membrane. Next, at the end of the antibody immobilized membrane which is an opposite side of the colloidal gold antibody holding pad, the absorption pad (a cellulose•glass membrane cut into 20 mm×250 mm (CF6, Whatman Ltd.)) was grafted overlapping in widthways so that it overlapped by approximately 5 mm with the membrane.

A plurality of immunochromatography strips of 7 mm×60 mm were prepared schematically as shown in FIG. 1 and FIG. 2 by cutting these overlapped and grafted members (immunochromatography body member) in parallel with the short side so that the width was made to be 7 mm in a direction perpendicular to the detection site and the control site using a guillotine cutter (CM4000, NIPPN/TechnoCluster, Inc.). These were made to be an immunochromatography test kit.

(1-5) Cleaning Liquid

The amplification liquid A-1 described in following (1-6) was used.

(1-6) Preparation of Silver Amplification Liquid (1-6-1) Preparation of Amplification Liquid A-1 (Solution Containing Reducing Agent Component for Silver Ions)

40 mL of 1 mol/L aqueous solution of iron nitrate made by dissolving iron (III) nitrate nonahydrate (Wako Pure Chemical Industries, Ltd., 095-00995) in water, 10.5 g of citric acid (Wako Pure Chemical Industries, Ltd., 038-06925), 0.1 g of dodecylamine (Wako Pure Chemical Industries, Ltd., 123-00246), and 0.44 g of surfactant $C_9H_{19}-C_6H_4-O-(CH_2CH_2O)_{50}H$ were dissolved in 325 g of water. When these were all dissolved, 40 mL of nitric acid (10 mass %) were added stirring using a stirrer. 80 mL of this solution were weighed out and 11.76 g of iron (II) ammonium sulfate hexahydrate (Wako Pure Chemical Industries, Ltd., 091-00855) was added, and this was made to be amplification liquid A-1.

(1-6-2) Preparation of Amplification Liquid A-2 (Solution Containing Silver (Ion)-Containing Compound)

Water was added to 10 mL of silver nitrate solution (containing 10 g of silver nitrate) so that the total amount became 100 g and amplification liquid A-2 (10 mass % aqueous solution of silver nitrate) was prepared.

(1-7) Casein Hydrolyzate (1-7-1) Preparation of Casein Hydrolyzate

1 L of 5 mass % casein solution (one or more of αS1 casein, αS2 casein, β casein, or κ casein are included) was stirred using a stirrer and 84.2 mL of pure water was added. Thereto, 10 mL of solution in which lysyl endopeptidase (R) (Wako Pure Chemical Industries, Ltd., for biochemistry, 125-02543) was dissolved in dissolution buffer (0.1 M phosphoric acid Na, 2 mM EDTA.2Na, pH 7.8) to be 0.05 AU/mL was added. This was allowed to stand for 10 days in a thermostat of 37° C. and was used as the casein hydrolyzate.

10 μL of NuPAGE LDS sample buffer (4×) (Life Technologies Corporation) was added to 30 μL of casein hydrolyzate. This solution was treated by heating at 70° C. for 10 minutes and the resultant was injected to NuPAGE Bis-Tris gel (Life Technologies Corporation). Electrophoresis was performed for 40 minutes at 200 V using XCell SureLock Mini-cell (Life Technologies Corporation) and power supply (Life Technologies Corporation) using a running buffer in which NuPAGE MES SDS running buffer (20×) (Life Technologies Corporation) is 20 times diluted with pure water. The resultant was stained for 1 hour at room temperature using InstantBlue (Former Novexin Ltd.) as a gel staining liquid and was repeatedly cleaned by replacing pure water until the color of the background was decolorized. After that, it was imaged using LAS-4000 (Fujifilm Corporation), the band concentration was integrated using analysis software Multi Gauge, and the molecular weight and the content ratio of the protein was quantified. The result was that 50% or more of the total protein amount was in the molecular weight range of greater than or equal to 1 kD and less than or equal to 15 kD and the molecular weight range of the main was greater than or equal to 1 kD and less than or equal to 15 kD.

(1-7-2) Preparation of Casein Hydrolyzate of which Acid Insoluble Substance is Removed 4 mL of enzyme hydrolyzed casein made from (1-7-1) was adjusted to pH 3.0 using 2 mol/L of hydrochloric acid and was suspended. After leaving to stand for 5 minutes at 4° C., centrifugation was performed for 10 minutes at 9,000×g and 4° C. Supernatant was collected so as not to disturb the precipitate and the casein hydrolyzate of which acid insoluble substance is removed was prepared.

(2) Evaluation (Setting of Device)

Figure 3:
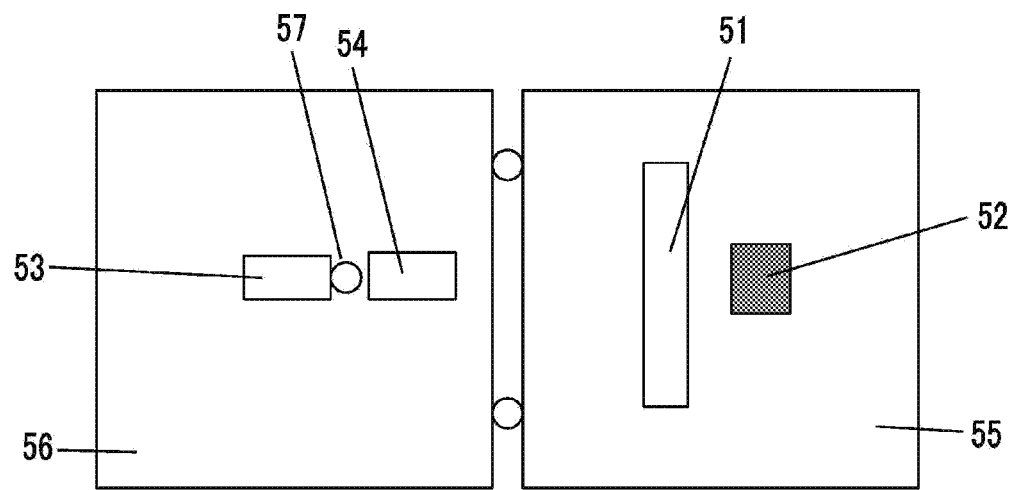
FIG. 3 schematically shows one aspect of an immunochromatography kit which can be used in the present invention. 51 represents the first insoluble carrier (the immunochromatography strip) shown in FIG. 1

An experiment was performed using the immunochromatography kit shown in FIG. 3. The immunochromatography strip (51) prepared by (1-4) was mounted to a first device component (55) of FIG. 3 and the second insoluble carrier (53) (glass fiber pad cut into 15 mm×12 mm (GF/F, GE Healthcare, Ltd.)) as the cleaning liquid addition pad and the third insoluble carrier (54) (glass fiber pad cut into 15 mm×12 mm (GF/F, GE Healthcare, Ltd.)) as a water supply pad were attached to a second device component (56), respectively.

(Adhesion•Development of Antibody Liquid)

As the test sample (analyte liquid), an antibody diluted solution in which BD Flu examen control A+B− (Becton, Dickinson and Company) is dissolved in PBS buffer containing 1 mass % BSA was prepared.

Detection limit of BD Flu examen control A+B− by commercially available immunochromatography detection kit "Capilia FluA·B" (Alfresa Pharma Corporation) was 1/40, however, this positive control liquid was diluted to 1/3200 using PBS buffer containing 1 mass % BSA and was used as a simulated positive analyte liquid 1/3200. 65 µl of the analyte liquid was added dropwise uniformly to the sample addition pad of the immunochromatography strip prepared by (1-4) and was left to stand for 2 minutes.

(Cleaning)

After the analyte liquid was added dropwise, left to stand for 2 minutes and developed as described above, 150 µl of amplification liquid (A-1) containing the reducing agent component prepared by (1-6-1) was placed in a liquid storage pod (52) of the first device component (55) shown in FIG. 3. The second device component (56) was closed facing toward the first device component (55), the tip of the second insoluble carrier (53) (the cleaning liquid addition pad) was immersed in amplification liquid (A-1) containing the reducing component of the liquid storage pod (52), and the second insoluble carrier (53) (the cleaning liquid addition pad) and the third insoluble carrier (54) (the water supply pad) was mounted to the immunochromatography strip prepared by (1-4), which is the first insoluble carrier (51), from the side in the longitudinal direction. Then, amplification liquid (A-1) containing the reducing agent component was developed on the immunochromatography strip and the liquid was delivered for 2 minutes. From this procedure, the immunochromatography strip was immersed in amplification liquid (A-1) containing the reducing agent component and the material which was not specifically adsorbed was further washed out.

(Signal Amplification by Amplification Liquid)

Amplification Liquid (A-2) containing silver ions prepared by (1-6-2) from an adhesion hole (57) installed in the second device component (56) was added dropwise, and the colloidal gold label adsorbed to the detection site was amplified for 1 minute. After the amplification, the immunochromatography strip which is the first insoluble carrier (51) was taken out and washed with water for 1 minute.

(Measurement of Line Concentration)

This immunochromatography strip was measured using a concentration measuring device for immunochromatography ICA-1000 (Hamamatsu Photonics) and the absorbance difference between the background and the detection site (ΔOD, mABS unit) was determined and evaluated.

(Analyte Liquid)

As the Blank analyte solution, PBS buffer containing 1 mass % BSA was prepared and as the ×1/3200 simulated positive analyte, BD Flu examen control A+B− (Becton, Dickinson and Company) dissolved in PBS buffer containing 1 mass % BSA was prepared.

Comparative Example 1

No Casein

The Blank analyte and the simulated positive analyte themselves were used as the analyte liquid.

Comparative Example 2

Casein Added

Casein was added to the Blank analyte and the simulated positive analyte so that the final concentration became 1 mass %.

Example 1

Casein Hydrolyzate Added

Casein hydrolyzate was added to the Blank analyte and the simulated positive analyte so that the final concentration became 1 mass %.

Example 2

Casein hydrolyzate of which acid insoluble substance was removed was added to the Blank analyte and the simulated positive analyte so that the final concentration became 1 mass %.

False-positives in the Blank analyte were evaluated such that a case in which a measurement was impossible due to unevenness was "−", a case in which 1 mABS to 50 mABS with regard to false-positive was "A" and a case in which 51 mABS to 100 mABS with regard to false-positive was "B". Also, the unevenness on the amplification surface in the Blank analyte was evaluated such that a case which there was no unevenness was "A", a case in which there was small unevenness was "B", and a case in which there was unevenness was "C". Also, the concentration of the line of the simulated positive analyte was evaluated such that a case in which 1 mABS to 50 mABS was "A" and a case in which an evaluation was impossible due to false-positive or a measurement was impossible due to unevenness was "−".

The results are shown in Table 1 below.

In Comparative Example 1, strong false-positive occurred.

In Comparative Example 2, amplification unevenness occurred therefore the concentration of the line could not be measured.

In Example 1, false-positive was highly reduced, and also the concentration of the line became significantly detectable with regard to the Blank in the simulated positive analyte 1/3200. However, small amplification unevenness occurred.

In Example 2, false-positive was highly reduced, and also the concentration of the line became significantly detectable with regard to the blank in the simulated positive analyte 1/3200.

Also, the average particle size at the time of the detection when detected in Example 1 was calculated according to "9. Method of Calculating Average Particle Size at the Time of Detection" and the size was 6 to 8 μm.

TABLE 1

| | | | | | | |
|---|---|---|---|---|---|---|
| | | | Comparative Example 1 No casein | Comparative Example 2 Casein added | Example 1 Casein Hydrolyzate Added | Example 2 Casein hydrolyzate of which acid insoluble substance was removed added |
| | | False-positive in Blank analyte | | | | |
| Blank Analyte | False-positive | | B 79 mABS | — Measurement impossible due to unevenness | A 22 mABS | A 20 mABS |
| | Evaluation of unevenness on Amplification Surface | | A No unevenness | C Unevenness | B Small unevenness occurred | A No unevenness |
| Simulated Positive Analyte 1/3200 | Concentration of Line | | — Evaluation impossible due to false-positive | — Measurement impossible due to unevenness | A 47 mABS | A 45 mABS |

What is claimed is:

1. An immunochromatography method comprising:
   in a state where a complex of a test substance and a labeling substance containing a metal coupled with a first binding substance for the test substance is formed, the complex is developed on an insoluble carrier in presence of a protease hydrolyzate of protein;
   wherein the test substance and the labeling substance are captured at a detection site of the insoluble carrier containing (a) a substance which has a binding property to the first binding substance for the test substance or (b) a second binding substance for the test substance; and
   detecting the test substance by amplifying the labeling substance captured,
   wherein:
   the protease hydrolyzate of protein is a hydrolyzate which does not precipitate insoluble components under acidic conditions, and
   the protease hydrolyzate of protein is a protein hydrolyzate obtained by adding an acid to the protease hydrolyzate of protein, adjusting the pH to 4 or less and removing the precipitates precipitated.

2. The immunochromatography method according to claim 1, wherein the molecular weight range of the protease hydrolyzate of protein is 0.1 kD to 15 kD.

3. The immunochromatography method according to claim 1,
   wherein the protease hydrolyzate of protein is a protease hydrolyzate of casein.

4. The immunochromatography method according to claim 2,
   wherein the protease hydrolyzate of protein is a protease hydrolyzate of casein.

5. The immunochromatography method according to claim 3,
   wherein the casein is one or more casein selected from αS1casein, αS2casein, βcasein, or κcasein.

6. The immunochromatography method according to claim 1,
   wherein at least one of the first binding substance and the second binding substance is an antibody.

7. The immunochromatography method according to claim 2,
   wherein at least one of the first binding substance and the second binding substance is an antibody.

8. The immunochromatography method according to claim 1, further comprising:
   amplifying the labeling substance captured using an amplification liquid containing a silver-containing compound and a reducing agent for silver ions.

9. The immunochromatography method according to claim 2, further comprising:
   amplifying the labeling substance captured using an amplification liquid containing a silver-containing compound and a reducing agent for silver ions.

10. The immunochromatography method according to claim 1,
wherein a cleaning liquid is provided on the insoluble carrier after the complex is developed on the insoluble carrier in presence of the protease hydrolyzate of protein.

11. The immunochromatography method according to claim 2,
wherein a cleaning liquid is provided on the insoluble carrier after the complex is developed on the insoluble carrier in presence of the protease hydrolyzate of protein.

12. An immunochromatography kit, comprising:
a labeling substance containing a metal coupled with a first binding substance for a test substance,
a protease hydrolyzate of protein, and
an insoluble carrier containing a material which has a binding property to the first binding substance for the test substance or a second binding substance for the test substance.

13. The immunochromatography kit according to claim 12,
wherein at least one of the first binding substance and the second binding substance is an antibody, and further comprising an amplification liquid containing a silver-containing compound and a reducing agent for silver ions.

14. The immunochromatography method according to claim 6,
wherein the second binding substance is an antibody.

15. The immunochromatography kit according to claim 13, wherein the second binding substance is an antibody.

16. The immunochromatography method according to claim 1, wherein the (a) or (b) component of the insoluble carrier are contained in a material with a binding property to either (a) or (b).

* * * * *

SEQUENCE LISTING

<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: S1 casein derived peptide

<400> SEQUENCE: 1

Tyr Leu Gly Tyr Leu Glu Gln Leu Leu Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: S1 casein derived peptide

<400> SEQUENCE: 2

Phe Phe Val Ala Pro Phe Pro Glu Val Phe Gly Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: S1 casein derived peptide

<400> SEQUENCE: 3

His Gln Gly Leu Pro Gln Glu Val Leu Asn Asn Leu Leu Arg
1               5                   10

<210> SEQ ID NO 4
<211> LENGTH: 8
<212> TYPE: PRT
<213> ORGANISM: Artificial Sequence
<220> FEATURE:

-continued

```
<223> OTHER INFORMATION: S2 casein derived peptide

<400> SEQUENCE: 4

Phe Ala Leu Pro Gln Tyr Leu Lys
1               5

<210> SEQ ID NO 5
<211> LENGTH: 7
<212> TYPE: PRT
<213> ORGANISM: Artificial Sequence
<220> FEATURE:
<223> OTHER INFORMATION: S2 casein derived peptide

<400> SEQUENCE: 5

Ala Val Pro Tyr Pro Gln Arg
1               5

<210> SEQ ID NO 6
<211> LENGTH: 9
<212> TYPE: PRT
<213> ORGANISM: Artificial Sequence
<220> FEATURE:
<223> OTHER INFORMATION: S2 casein derived peptide

<400> SEQUENCE: 6

Tyr Pro Val Glu Pro Phe Thr Glu Arg
1               5

<210> SEQ ID NO 7
<211> LENGTH: 10
<212> TYPE: PRT
<213> ORGANISM: Artificial Sequence
<220> FEATURE:
<223> OTHER INFORMATION: S2 casein derived peptide

<400> SEQUENCE: 7

Tyr Ile Pro Ile Gln Tyr Val Leu Ser Arg
1               5                   10
```